United States Patent [19]
Horn

[11] Patent Number: 5,869,323
[45] Date of Patent: Feb. 9, 1999

[54] ARRANGEMENT FOR AIR PURIFICATION; AND METHOD

[75] Inventor: Robert Jeffrey Horn, Eagan, Minn.

[73] Assignee: Basys Technologies, Inc., Minneapolis, Minn.

[21] Appl. No.: 788,595

[22] Filed: Jan. 22, 1997

Related U.S. Application Data

[62] Division of Ser. No. 414,728, Mar. 31, 1995, Pat. No. 5,635,394.

[51] Int. Cl.$^6$ .............................. A61L 9/01; B01D 47/00
[52] U.S. Cl. ...................... 435/266; 435/262; 435/286.6; 435/296.1; 55/223; 55/233
[58] Field of Search ..................... 435/266, 262, 435/286.6, 296.1; 55/223, 233

[56] References Cited

U.S. PATENT DOCUMENTS

| | | |
|---|---|---|
| 2,200,581 | 5/1940 | Pruss et al. . |
| 3,216,905 | 11/1965 | Baptist . |
| 3,269,542 | 8/1966 | Renzi et al. . |
| 3,376,219 | 4/1968 | Silvey . |
| 3,445,182 | 5/1969 | Tomany . |
| 3,828,525 | 8/1974 | Copa et al. . |
| 4,036,750 | 7/1977 | Jaros et al. ................................ 210/27 |
| 4,053,396 | 10/1977 | Trense et al. .............................. 210/17 |
| 4,088,571 | 5/1978 | Helgesson . |
| 4,186,085 | 1/1980 | Savage ...................................... 210/27 |
| 4,207,179 | 6/1980 | McCarthy et al. .......................... 210/7 |
| 4,225,381 | 9/1980 | Ishikawa et al. . |
| 4,230,801 | 10/1980 | Gutnick et al. .......................... 435/101 |
| 4,290,894 | 9/1981 | Torok et al. ............................. 210/661 |
| 4,608,160 | 8/1986 | Zoch ....................................... 210/114 |
| 4,662,900 | 5/1987 | Ottengraf . |
| 4,734,111 | 3/1988 | Hoffmann et al. ....................... 435/266 |
| 4,806,148 | 2/1989 | Ottengraf . |
| 4,816,158 | 3/1989 | Shimura et al. ......................... 210/610 |
| 4,961,763 | 10/1990 | Thompson et al. ..................... 435/266 |
| 5,120,435 | 6/1992 | Fink ........................................ 210/192 |
| 5,238,658 | 8/1993 | Makioka et al. .......................... 96/131 |
| 5,279,963 | 1/1994 | Hobby ..................................... 435/266 |
| 5,409,834 | 4/1995 | Birdwell ................................. 435/299.1 |

FOREIGN PATENT DOCUMENTS

| | | |
|---|---|---|
| 2558256 | 7/1977 | Germany . |
| 2643211 | 4/1978 | Germany . |

OTHER PUBLICATIONS

Allen et al., "Techniques for Treating Hazardous Wastes to Remove Volatile Organic Constiuents", *Journal of Air Pollution Control Assoc,* 45(8):841–848 (Aug. 1985).

Angelo, "Sludge Plant's New (s)cents", *ENR,* p. 37 (Jan. 30, 1995).

Apel et al., "Removal of a–Pinene from Off–Gases by Biofiltration", 95–TP9C.07 Presentation at 88th Annual Meeting & Exhibition of Air & Waste Management Association, San Antonio, TX, pp. 1–16 (Jun. 1995).

Apel et al., "Removal of Gasoline Vapors from Air Streams by Biofiltration", EGG–WTD–10714, Idaho National Engineering Laboratory, EG&G Idaho, Inc. Idaho Falls, Idaho. (Mar. 1993).

Baltzis et al. "A Study on the Response of Biofilters to Shock–Loading", 94–RP115B.02, Air & Waste Management 87th Annual Meeting & Exhibition, Cincinnati, OH, pp. 1–14 (Jun. 19–24, 1994).

(List continued on next page.)

*Primary Examiner*—Marian C. Knode
*Assistant Examiner*—Ali R. Salimi
*Attorney, Agent, or Firm*—Merchant, Gould, Smith, Edell, Welter & Schmidt, P.A.

[57] ABSTRACT

A method and arrangement for conducting air filtration by biofilter operation is provided. The arrangement generally includes at least one bioreactor bed, through which air to be purified is passed. Preferably the arrangement is configured so that air flow through each tank is from the top downwardly. In general, the biofiltration operation is conducted under pressures of less than ambient, to advantage.

13 Claims, 4 Drawing Sheets

OTHER PUBLICATIONS

Barr et al., "Mechanisms White Rot Fungi Use to Degrade Pollutants", *Environ. Sci. Technol.,* 28(2):79A–87A (1994) (no month cited on the reference).

Bebutez et al., "Kinetics of the Degradation of Toluene and Ethylbenzene in a Compost–Based Biofilter", 95–TP9C.06, Air & Waste Management 88th Annual Meeting & Exhibition, San Antonio, TX, pp. 1–15 (Jun. 18–23, 1995).

H. Bohn et al., "Soil Bed Scrubbing of Fugitive Gas Releases", *J. Environ. Sci. Health,* A21(g):561–569 (1986) (no month cited on the reference).

H. Bohn, "Consider Biofiltration for Decontaminating Gases", *Chemical Engineering Progress,* 88:34–40 (Apr. 1992).

H. Bohn, "Soil Absorption of Air Pollutants", *J. Environ. Quality,* 1(4):372–377 (1972) (no month cited on the reference).

H. Bohn et al., "Soil Beds Weed Out Air Pollutants", *Chemical Engineering,* 95(6):73–76, (Apr. 25, 1988).

Chang et al., "A Simple Test to Determine the Applicability of Biofiltration to Waste Gas Treatment", 94–RA115A.03, Air & Waste Management 87th Annual Meeting & Exhibition, Cincinnati, OH, pp. 1–17 (Jun. 19–24, 1994).

Croonenberghs et al., "Use of Bioscrubbing to Control Ethanol Emissions", 94–RP115B.06, Air & Waste Management 87th Annual Meeting & Exhibition, San Antonio, TX, pp. 1–10 (Jun. 19–24, 1994).

Duncan et al., "Pollutant Removal from Wood and Coal Flue Gases by Soil Treatment", *Control Technology News,* 32(11):1175–1179 (Nov. 1982).

Ergas et al., "Biodegradation Technology for Volatile Organic Compound Removal from Airstreams, Phase I: Performance Verification ", U.S. Department of Commerce, National Technical Information Service, Springfield, VA (May 1992).

Ergas et al., "Spatial Distribution of Microbial Populations in Biofilters", Air & Waste Management 87th Annual Meeting & Exhibition, Cincinnati, OH pp. 1–9 (Jun. 19–24, 1994).

Fouhy et al., "Biology Boosts Waste Treatment: Water and Waste Gas: Expanding the Microbial Menu", *Chemical Engineering,* pp. 30–32 (Feb. 1994).

Fouhy, "Cleaning Waste Gas, Naturally", *Chemical Engineering,* 99(12):41–46 (Dec. 1992).

Griffin et al., "Biofiltration: Weighing the Technology's Cost Benefits", *Environmental Protection,* pp. 17–18 (Jul. 1995).

Gschwandiner et al., "Project Summary: Controlling Odorous Emissions from Iron Foundries", United States Environmental Protection Agency, pp. 1–3 (May 1992).

Hammervold et al., "Experimental Study of the Sorptive Slurry Bioscrubber for Acetone Emissions", Air & Waste Management 88th Annual Meeting & Exhibition, San Antonio, TX, pp. 1–14 (Jun. 18–23, 1995).

Hall et al., "Interim Private Water Well Remediation Using Carbon Adsorption", *GWMR,* pp. 77–83 (Winter 1987).

Heuckeroth, "Biofilters Provide New Options to Control Air Emissions", *The National Environmental Journal,* pp. 20–22 (Nov./Dec. 1993).

Hodge et al., "Modeling Removal of Air Contaminants by Biofiltration", *Journal of Environmental Engineering,* 121(1):21–32 (Jan. 1995).

Kamarthi et al., "Bench–Scale Evaluation of Air Pollution Control Technology Based on Biological Treatment Process", Air & Waste Management 87th Annual Meeting & Exhibition, Cincinnati, OH, pp. 1–16 (Jun. 19–24, 1994).

Kampbell et al., "Removal of Volatile Aliphatic Hydrocarbons in a Soil Bioreactor", *Control Technology,* 37(10):1236–1239 (Oct. 1987).

Kardono et al., "Elimination of Benzene Using a Compost Biofilter", Air & Waste Management 88th Annual Meeting & Exhibition, San Antonio, TX pp. 1–14 (Jun. 18–23, 1995).

Kardono et al., "Biofiltration Control of Volatile Hydrocarbon Emissions:n–Butane", Air & Waste Management 87th Annual Meeting & Exhibition, Cincinnati, OH, pp. 1–16 (Jun. 19–24, 1994).

Kavanaugh et al., "Design of Aeration Towers to Strip Volatile Contaminants from Drinking Water", *Journal of A.W.W.A.,* pp. 43–51, published on a date prior to May 29, 1992 (no month cited on the reference).

Kirchner et al., "Biological Purification of Waste Gases by Means of Immobilised Bacteria (Monocultures)", Air & Waste Management 87th Annual Meeting & Exhibition, Cincinnati, OH, pp. 1–14 (Jun. 19–24, 1994).

Kissel et al., "Potential Emissions of Volatile and Odorous Organic Compounds from Municipal Solid Waste Composing Facilities", *Biomass and Bioenergy,* 3(3–4):181–194 (1992) (no month cited on the reference).

van Langenhove et al., "Inhibitory Effects of $SO_2$ on Biofiltration of Aldehydes", *Water, Air and Soil Pollution,* 47:81–86 (Sep. 1989).

Leson et al., "A Status Overview of Biological Air Pollution Control", Air & Waste Management Association 88th Annual Meeting & Exhibition, San Antonio, TX, pp. 1–9 (Jun. 18–23, 1995).

Leson et al., "Experiences with a Full–Scale Biofilter for Control of Ethanol Emissions", Air & Waste Management 88th Annual Meeting & Exhibition, San Antonio, TX, pp. 1–11 (Jun. 18–23, 1995).

Leson et al., "Biofiltration: An Innovative Air Pollution Control Technology for VOC Emissions", Air Waste Management Assoc. 41(8):1045–1054 (Aug. 1991).

McGrath et al., "Hollow Fiber Membrane Bioreactor for Control of Volatile Organic Compound Emissions", Air & Waste Management 88th Annual Meeting & Exhibition, San Antonio, TX, pp. 1–15 (Jun. 18–23, 1995).

Michal, "An Overview: Air Stripping of Organic Compounds: Air Stripping in Water Treatment Today", *Pollution Equipment News,* pp. 103–110 (Aug. 1988).

Montgomery, "Gas Transfer", *Waste Treatment Principles and Design,* John Wiley and Sons, Inc., pp. 237–261, (1985) (no month cited on the reference).

Morgenroth et al., "Nutrient Limitation in a Compost Biofilter Degrading Hexane", Air & Waste Management 88th Annual Meeting & Exhibition, San Antonio, TX, pp. 1–16 Jun. 18–23, 1995.

Parten, "Using Waste Wood Chips to Treat Septage", *BioCycle,* pp. 74–76 (Apr. 1994).

Perry, "Liquid–Gas Systems", *Chemical Engineers' Handbook,* Section 18, pp. 18–22 through 18–25, published on a date prior to May 29, 1992. (no date/month cited on the reference).

Paul et al., "Biologic Filtration, a Removal Method of Foundry's Waste Air", Air & Waste Management 88th Annual Meeting & Exhibition, San Antonio, TX, pp. 1–16 (Jun. 18–23, 1995).

Prokop et al., "Control Technology News: Soil Bed System for Control of Rendering Plant Odors", *Journal of the Air Pollution Control Association*, pp. 1332–1338 (1985) (no month cited on the reference).

Ramsey et al., "Control of Paint Solvent Emissions from a Tankcar Lining Operation Through the Use of a Microbial Air Scrubber", Air & Waste Management 88th Annual Meeting & Exhibition, San Antonio, TX, pp. 1–10 ( Jun. 18–23, 1995).

Santoleri, "Design and Operating Problems of Hazardous Waste Incinerators", *Environmental Progress*, 4(4):246–251 (Nov. 1985).

Seed et al., "Biofiltration of BTEX–Contaminated Gas Streams: Laboratory Studies", Air & Waste Management 87th Annual Meeting & Exhibition, Cincinnati, OH, pp. 1–14 (Jun. 19–24, 1994).

Singleton et al., "Three Case Studies of Biofiltration for the Removal of BTEX Compounds, $H_2S$, and Organic Reduced Sulfur Compounds", Air & Waste Management 88th Annual Meeting & Exhibition, San Antonio, TX, pp. 1–24 (Jun. 18–23, 1995).

Sorial et al., "Evaluation of the Performance of Trickle Bed Biofilters — Impact of Periodic Removal of Accumulated Biomass", Air & Waste Management 87th Annual Meeting & Exhibition, Cincinnati, OH, pp. 1–16 (Jun. 19–24, 1995).

Tonga et al., "Field–Pilot Results of Styrene Biodegradation Using Biofiltration: A Case Study", A. Presented at the 48th Annual Purdue University Industrial Waste Conference, Purdue University, West Lafayette, Indiana, pp. 1–16 (May 11, 1993).

Tonga et al., "A Comparative Study of Biofilter and Biotrickling Filter Performance for Isopentane Removal", Air & Waste Management 87th Annual Meeting & Exhibition, Cincinnati, OH, pp. 1–15 (Jun. 19–24, 1994).

Vogel, "Air Emission Control at Hazardous Waste Management Facilities", *Journal of the Air Pollution Control Association*, 35(5):558–566 (May 1985).

Webster et al., "Study of Biofiltration for Control of VOC and Toxics Emissions from Wastewater Treatment Plants Phse II Bench–Scale Experiments", Air & Waste Management 88th Annual Meeting & Exhibition, San Antonio, TX, pp. 1–13 (Jun. 18–23, 1995).

Williams et al., "Biofiltration for the Control of Odorous and Volatile, Organic Compound Emissions in High Temperature Industrial Applications", Air & Waste Management 88th Annual Meeting & Exhibition, San Antonio, TX, pp. 1–14 (Jun. 18–23, 1995).

Yang et al., "Oxidative Destruction of Carbon Disulfide Vapors Using Biofiltration", Air & Waste Management 87th Annual Meeting & Exhibition, Cincinnati, OH, pp. 1–13 (Jun. 19–24, 1994).

PRODUCT BROCHURES and ADVERTISEMENTS:

"Anaerobic Bioremediation System for Degradation of TNT and Other Energetics", J.R. Simplot Company, Pocatello Idaho; Envirogen, Inc. Canton, Massachusetts; published Mar. 1994.

Advertisement "Bioton® The World Leader in Biofiltration for Optimum VOC and Odor Control", PPC Biofilter, Longview, TX (no date cited on the reference).

"CECASORB™ Adsorbent Canisters" Product Brochure, Atochem North America, published on a date prior to May 29, 1992 (no date cited on the reference).

"Drums and Systems for Carbon Adsorption" Product Brochure, Continental Environmental Services, Gainesville, Florida, published on a date prior to May 29, 1992 (no date cited on the reference).

"Envirogen Impact Statement" Product Brochure, Envirogen, Inc. Canton, Massachusetts (no date cited on the reference).

"Environmental Instruments Activated Carbon" Product Brochure, Environmental Instruments, published on a date prior to May 29, 1992 (no date cited on the reference).

"Biofilter Systems for the Treatment of VOCs and Odors" Product Brochure, Envirogen, Inc., Princeton Research Center, Lawrenceville, NJ (no date cited on the reference).

"Bio–Trickling Technology Treats High Acid Concentration Exhaust Gases" Product Brochure, Ambient Engineering, Inc., Matawn, NJ (no date cited on the reference).

"Bohn Mobile Biofilters" Product Brochure, Bohn Biofilter Corporation, Tucson, AZ (no date cited on the reference).

"Environmentally Benign Biofiltration System for the Reduction of VOCs and Complex Odors" Product Brochure, EG&G Biofiltration, Saugerties, NY (1994) (no month cited on the reference).

"H2 Oil Recovery Equipment Air Stripping Tower" Product Brochure, Bend, Oregon, (1990) (no month cited on the reference).

"Envirogen: Innovative Solutions for Environmental Problems" Corporate Brochure, Envirogen, Inc., Lawrenceville, NJ and Vapex Environmentla Technologies, Inc., Canton, Massachusetts (no date cited on the reference).

"Introducing Aquazorb™ Activated Carbon Adsorption System" Product Brochure, Hadley Industries, Ludington, MI, published on a date prior to May 29, 1992 (no date cited on the reference).

"ORS TCLP Systems in Operation at Bulk Terminals" Advertisement, ORS Environmental Equipment, Greenville, NH (no date cited on the reference).

"Portable Airstripping Tower" Product Brochure, Carbon Air Services, Inc., Hopkins, MN, published on a date prior to May 29, 1992 (no date cited on the reference).

"Selection Criteria for Granular Activated Carbon (GAC)" Product Brochure, TIGG Corporation, Pittsburgh, PA, published on a date prior to May 29, 1992 (no date cited on the reference).

"Soil Bed Engineering" Product Brochure, Bohn Biofilter Corporation, Tucson, AZ, (no dated cited on the reference).

"Groundwater Technology Charts Course Beyond USTs", Interview with Richard Brown, *The Bioremediation Report*, pp. 2–16 (Apr. 1995).

"Strippers (Aeration Towers)" Product Brochure, Ceilcote, published on a date prior to May 29, 1992 (no date cited on the reference).

"TM–100: Protection for Activated Carbon Water–Treatment Systems" Product Brochure, Technical Minerals, Inc., published on a date prior to May 29, 1992 (no date cited on the reference).

"VOC/Odor Treatment with the BIKOVENT® System" Product Brochure, Biofiltration, Inc., Lauderdale by the Sea, Flordia (no date cited on the reference).

"New Solutions to Hazardous Waste Problems: Envirogen Announces Successful Demonstration of Biological Air Pollution Control Technology" News Release; Envirogen News, Envirogen, Inc., Lawrenceville, NJ (no date cited on the reference).

"Description and Functional Explanation for the Nelson Bilge Boy™ Oil/Water Separators" Product Brochure, Nelson Division–Environmental Systems, Stoughton, WI, published on a date prior to May 29, 1992 (date stamp on reference is Sep 24, 1991).

"Megator S.O.R.A.S. Oily Water Separator" Product Brochure, published on a date prior to May 29, 1992 (no date cited on the reference).

"The New Solution to Oil Pollution: Clearwater Centrifugal Separator Systems" Product Brochure, Windholmen Services AS, Arendal, Norway, published on a date prior to May 29, 1992 (no date cited on the reference).

"The Hunter Oil Skimmer & The Hi–Rise LLS Liquid/Liquid Separator" Product Brochure, Action Engineering, Inc., Temple City, CA, published on a date prior to May 29, 1992 (no date cited on the reference).

"Biofiltration: A New Technology to Minimize Voc and Odor Emissions" Brochure, Scot Standefer and Chris Van Lith, PPC Biofilter, Longview, Texas (no date cited on the reference).

"For Cost–Efficient Odor Control and VOC Removal — PPC Biofilter," Product Brochure, PPC Biofilter, Longview, TX (no date cited on the reference).

ARRANGEMENT FOR AIR PURIFICATION; AND METHOD

This application is a divisional of U.S. patent application Ser. No. 08/414,728, filed Mar. 31, 1995, issued as U.S. Pat. No. 5,635,394 on Jun. 3, 1997.

FIELD OF THE INVENTION

The present invention relates to air filtration arrangements and processes. It particularly relates to arrangements which use, at least in part, biofiltration or bioreactor techniques for reduction of organic contaminants present in air.

BACKGROUND OF THE INVENTION

A wide variety of industries generate volatile and/or other air-borne generally non-particulate materials (for example odors, toxic organics, etc.) as byproducts. These include, for example, businesses such as: wood laminating; composting facilities; rendering plants; breweries; plastics molding; and, fiberglass manufacturing. In general, off-gases from processes conducted in such industries include substantial amounts of undesirable, and sometimes toxic, air-borne materials therein. Also, volatiles or other air-borne contaminants (such as odors) may be released from waste materials of these processes. It is generally undesirable that the process gases or volatiles from said activities be vented directly to the atmosphere. Indeed, environmental legislation, such as the 1990 Clean Air Act Amendment, limits the extent to which certain air-borne materials from such industries can be released.

A variety of techniques are available for removal of such materials from airstreams. One well-known method is incineration. Although incineration is effective, it is not, in many instances, a practical approach. First, there are generally high capital costs and operating costs associated with incineration. Secondly, there are generally air permit problems associated with implementation of new incinerators at various locations.

Activated carbon filters are sometimes used for removal of organics. Often generally involves passage of the air through a carbon filter. A problem is that in time the process generates contaminated carbon, which needs to be disposed of appropriately. Thus, while the technique has some positive effect for removing organics from air, it does not avoid the problem of disposal of contaminated materials. Also, activated carbon systems are not especially effective at removing certain organics which are relatively soluble in water.

Other types of systems which have found some beneficial use include biomass purification systems. In general, in such arrangements the contaminated airstream is passed through a bioreactor or biofilter including an active biomass. Bacteria within the biomass operate on the contaminating materials, often generating acceptable carbon dioxide off-gasses while consuming the organics. When the process is completed, the biomass, comprising the bacteria, typically does not contain substantial amounts of contaminants, and thus can be readily discarded, in safe manners.

While biomass arrangements provide significant advantage, to date they have not been as flexible and efficient as desired. What has been needed has been improvements in biomass air filtration arrangements, to enhance operation.

SUMMARY OF THE INVENTION

According to the present invention, a method is provided for conducting reduction in volatile and/or other air-borne contaminants in an airflow stream. Herein in this context the term "volatile and/or air-borne contaminants" includes within its scope odors, volatile and semi-volatile organics, and in some instances materials such as sulfur-containing materials, i.e. potentially almost any volatile or semi-volatile material carried in air flow stream. The method generally includes a step of directing air to be purified through at least one bioreactor bed, with the operation being conducted under a pressure of less than ambient. In general, the method is effected by directing the air through a bioreactor bed under a suction or draw, from downstream of the reactor bed. In preferred operations, the reactor bed and airflow conduits are configured so that airflow through the reactor bed is from the top downwardly. It certain preferred applications, after treatment in the bioreactor system, the air is exhausted through an exhaust stack. In some applications, before direction through the exhaust stack arrangement, the air is treated for reduction in moisture and particulates therein.

Also according to the present invention a bioreactor or biofilter arrangement for air treatment is provided. (Herein the terms "bioreactor" and "biofilter" are used interchangeably and without specific regard to whether the bed is operating to digest organics, filter material, or both.) The arrangement generally comprises: a first biofilter or bioreactor treatment tank having an air inlet and an air outlet; and, an air draw apparatus constructed and arranged to draw air through the first bioreactor treatment tank while maintaining a pressure within the first tank of less than ambient. This is generally done by utilizing a blower or fan (i.e. an air draw apparatus of some type) positioned downstream from the first bioreactor treatment tank, to draw air through the tank for treatment. Preferably the first bioreactor treatment tank is configured for downward air flow therethrough during treatment. In variations according to the present invention, the biofilter arrangement may include more than one bioreactor treatment tank. In some configurations, more than one tank is positioned in series, and in others the tanks are in parallel, and in some instances both. Preferably in the various arrangements, air flow is from the top downwardly through each tank, and the air draw apparatus is constructed and arranged for operation of each tank under a pressure of less than ambient.

In certain preferred systems, the bioreactor treatment tank includes at least one, one-foot thick, bioreactor bed therein. Preferably each tank includes at least a two-foot deep bioreactor bed or mass through which the air is passed. The at least two-foot deep bed in some systems may be separated into two or more sections, preferably each at least one-foot thick. Preferably each tank is at least one-foot deep, more preferably at least two-feet deep. Typically each tank will be 2.5 feet deep or more.

Arrangements according to the present invention may be utilized in a wide variety of systems, with various flow rates, etc. In some, relatively high flow rates, for example up to about 7500 ACFM (actual cubic feet per minute) or more, can be accomplished while utilizing plastic components for the treatment tanks and many of the pipes. In certain preferred systems, 9000 gallon PVC (polyvinyl chloride) tanks are used for the bioreactor tanks.

In some preferred embodiments, the tanks include a reactor bed comprising vertically stacked strata of more than one material. In certain preferred arrangements, the lower strata comprises rock, with certain strata above comprising a mixture of active bacteria-loaded material, such as peat and topsoil. By "active" in this context it is meant that the bacteria in the bed is active for reduction in the level of the volatile or other air-borne materials. In some arrangements, wood or bark chips (in some instances mixed with soil) are utilized in the bacteria-loaded mix to improve porosity.

In general, arrangments and techniques described herein can readily be applied to obtain 80% efficiency or greater, and often 90% efficiency or greater, at removing selected materials from air.

In certain preferred arrangements, the reactor bed comprises a plurality of sub-beds, oriented in a vertical stack, each comprising various strata as defined.

In the drawings, relative material thicknesses and component sizes may be shown exaggerated, for clarification.

BRIEF DESCRIPTION OF THE DRAWINGS

FIG. 2 being taken from the viewpoint of line 2—2, FIG. 1, and having portions broken away to show internal detail.

FIG. 4 being taken from the viewpoint of line 4—4, FIG. 3, and having portions broken away to show internal detail.

DETAILED DESCRIPTION OF THE INVENTION

I. General Principles of Improved Systems

Figure 1:
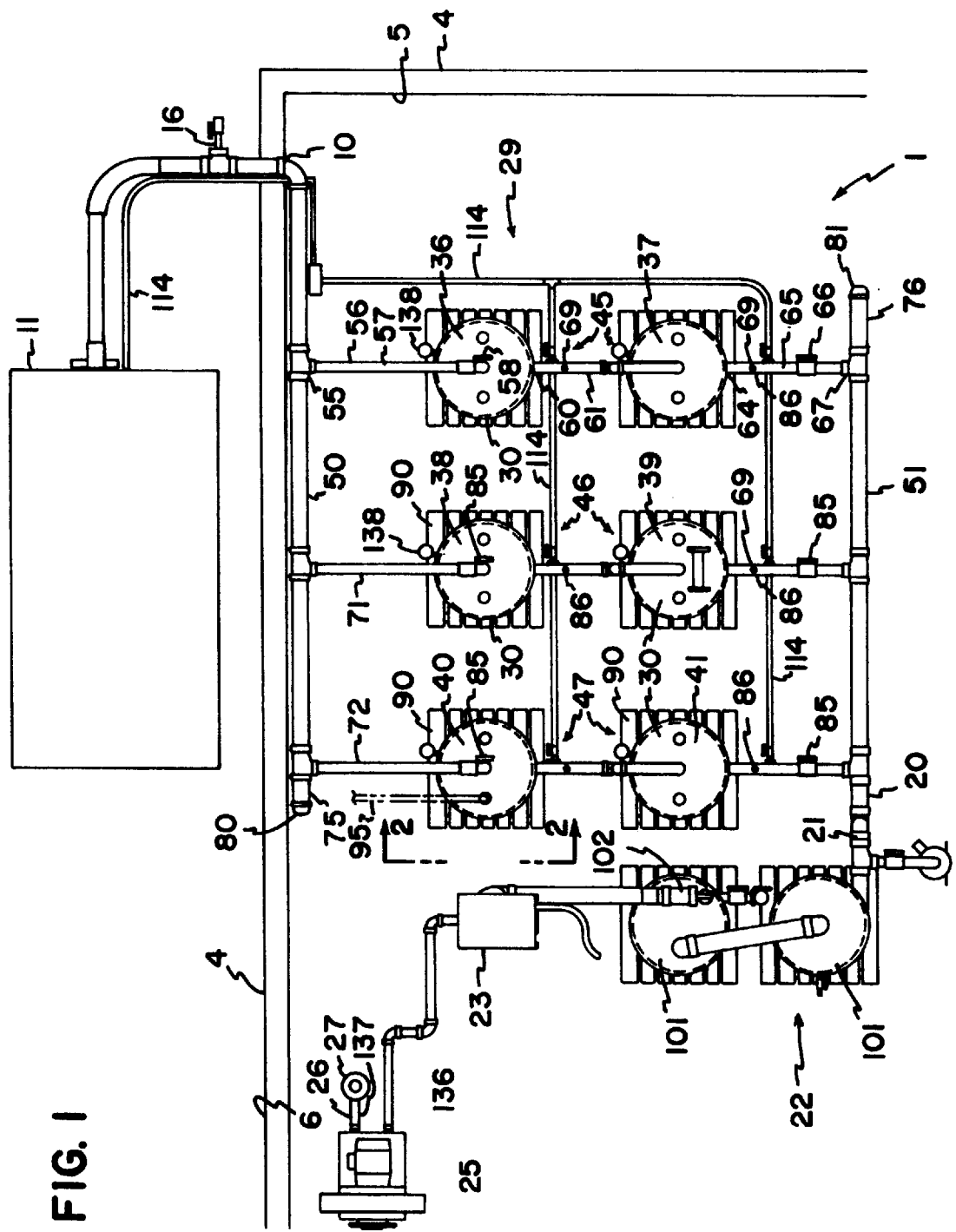
FIG. 1 is a top schematic representation of a biomass air filtration system according to the present invention.

Conventional biomass air filtration systems generally operate with a blower removing air from the room in which the contaminated process gases are generated, and forcing or driving the air through an air purification bed. Typically, the air is forced from the bottom upwardly through the bed or biomass reactor.

One of the reasons that the airflow in conventional systems is generally directed upwardly through the biomass, is because direction of the air, under pressure, through the biomass downwardly would tend to cause biomass packing and eventual build-up of an undesirable pressure head. Thus, in conventional forced air systems, upward flow is typical.

However, when the air is directed from the bottom up, loose material in the top of the bed in the reactor can easily be picked up in the air stream and blown through the system. Another problem with directing forced air upwardly through the biomass, is that the biomass may tend to "bump" or "burp" in time (to release pressure build up under the bed, by bed shift), increasing the likelihood of channelling; i.e. developing air flow bypass channels that reduce efficiency of air purification.

A variety of other problems are related with conventional biomass filters, which operate in the manner described above. For example, since the airflow through the biomass is under pressure, relatively large blowers are often needed to operate the systems. Also, any leak in the lines, tanks, etc. would be associated with a leak of contaminated material to the ambient, since the systems generally operate under internal pressure relative to ambient. This generates an associated need for relatively expensive tanks, line seals, etc., to help ensure against breakage or leaks. Further, it creates a potential for contamination at the site, should a leak occur; and, undesirable downtime, while the leak is being repaired. Further, it requires the development of biomass tanks of appropriate size and material that will resist undesirable "pack", to increase the pressure undesirably, under the pressure of airflow.

In addition, conventional systems have not been designed for efficient collection and removal of the airflow stream from the downstream side of the biomass. Rather, they have often been left open. This means that efficient discharge and dispersion of odoriferous off-gas streams have sometimes been problematic.

In general, the present disclosure concerns variations and improvements in biomass filters to significant advantage. A principal difference from typical prior arrangements is that, for arrangements according to the present invention, the equipment lines upstream of the biomass generally operate "under vacuum" relative to ambient. That is, rather than a forced air system directing the air into the biomass, a suction draw from downstream of the biomass is used, to pull the air through the biomass. This means that the airflow upstream from the biomass is not under substantial pressure, but rather is under a vacuum relative to ambient. Thus, a leak in the line upstream from the biomass will not generally result in leakage of contaminant to the atmosphere, but rather it will result in a draw of air from the atmosphere (ambient) into the system.

Secondly, in preferred arrangements disclosed herein, the airflow within the biomass is directed downwardly, rather than upwardly. This can reduce the likelihood that channelling such as that described above will result. Also, it can facilitate preferred water and nutrient flow. In addition, downstream equipment, such as blowers used to cause the airflow through the biomass, can be used to efficiently collect the air and direct it through a stack in an efficient manner for dispersion to the atmosphere.

Another advantage to certain of the preferred arrangements according to the present invention is that they are well adapted for generation of "modular" air cleaning systems. Thus, they can readily be expanded on site to accommodate variations in the processing. Further, they can be readily assembled from relatively inexpensive and readily obtained components. Indeed, in some applications otherwise discarded materials, such as spent agricultural tanks, can be used.

II. A Typical Improved System

In FIG. 1, a schematic depiction of an arrangement for implementing principles according to the present invention is depicted. While arrangements utilizing some or all of the advantageous principles of the present invention may be applied in a wide variety of specific systems, the particular system of FIG. 1 is typical and illustrative. From the following descriptions, variations will be understood.

Referring to FIG. 1, the reference numeral 1 generally indicates an air purification system according to the present invention. The particular system 1 of FIG. 1 is shown in relation to a building, with which it might be used. An exterior wall of the building is generally indicated at 4, with the interior indicated at 5 and the exterior at 6. For the system 1 of FIG. 1, the biomass is retained within the building, along with operating blowers and related equipment. In this manner, the environment of the biomass can be more readily controlled. It is not a requirement of systems according to the present invention, however, that the biomass be retained indoors. If needed, other means (for example heaters or insulated systems) may be used to provide a desirable and controlled environment for the biomass. Indeed, in some locations, average outdoor conditions can provide for a good, stable, biomass without further temperature or other environmental control.

Referring to FIG. 1, reference numeral 10 generally indicates an inlet for air to be treated, to the system, i.e. an air flow inlet. The air will generally have been removed from some process conducted upstream of inlet 10. For the particular arrangement of FIG. 1, upstream of inlet 10, a hooded evaporator unit 11 is shown. Thus, the particular application shown in FIG. 1 involves the purification (or reduction in the presence of) of organics from air that has been removed from a hooded evaporator unit.

The typical use of such an arrangement would be, for example, as follows. Indeed a test system was developed according to FIGS. 1 and 2, for such a use. In a process involving wood laminating, various washing steps may be conducted, periodically, of the equipment. The water wash would include organic contaminants and particulate contaminants therein. The waste water from the washing process might be evaporated, leaving nonvolatile residue. When the water is evaporated, some volatile and semi-volatile materials will be discharged to the air. A hooded evaporator such as that shown in FIG. 1 at 11 can be used to conduct this process. The bioreactor air purification system shown in FIG. 1, then, is operated to reduce the levels of volatile and semi-volatile materials in the off-gases resulting from operation of the hooded evaporator 11.

Also, upstream from inlet 10, is located a fresh air intake or bleed 16. This can be used to provide a fresh air flow through the biomass, or a partial bleed of fresh air into the biomass if desired. It is an advantage to the conduct of processes with arrangements according to the present invention, with the airflow stream at inlet 10 being generally under vacuum relative to ambient, that such inlets or bleeds can be efficiently utilized.

Still referring to FIG. 1, the reference numeral 20 generally indicates the air flow exit from the biomass purification system.

Downstream from exit 20, the air, after purification by the biomass, is directed through pipeline 21, through downstream water remover 22, filter 23 and air draw apparatus, i.e. blower 25. The exit or exhaust from blower 25 is generally indicated at 26. From this point, the air can be directed, for example, through a stack 27 for efficient dispersion in the atmosphere.

In general, blower 25 is constructed and arranged for operation to provide a suction or draw from pipeline 21. Thus, at least between inlet 10 and exit 20, system 1 is generally operated under vacuum relative to ambient, to advantage.

Still referring to FIG. 1, reference numeral 29 generally indicates the biomass filtration system 29. System 29 includes a plurality of air filter tanks 30. As will be apparent from the further detailed description, the tanks 30 are oriented so that selected tanks can be put on or off line as desired. Further, it will be apparent that the system can be readily expanded to accommodate still more tanks. Tanks 30 are sometimes referred to herein as "bioreactor treatment tanks" or "biofilter tanks". Preferably each tank has a top, a bottom and a sidewall arrangement, and each is at least one-foot deep, more preferably at least two feet deep. Typically each is greater than 2.5 feet deep.

For the arrangement shown in FIG. 1, the tanks 30 are oriented in three pairs of two tanks, each pair being in parallel with the other two pairs, and with the individual tanks in each pair being oriented in series relative to one another. Thus, arrangement 29 comprises tanks 36, 37, 38, 39, 40 and 41, with tanks 36 and 37 oriented in series relative to one another, tanks 38 and 39 oriented in series relative to one another, and tanks 40 and 41 oriented in series relative to one another. Further, the pair of tanks 45 comprising tanks 36 and 37 is oriented in parallel to pair 46 (comprising tanks 38 and 39) and also in parallel to pair 47 (comprising tanks 40 and 41).

In general, the inlet feed pipeline or manifold for pairs 45, 46 and 47 is indicated generally at 50. The outlet feed pipeline or manifold for pairs 45, 46 and 47 is indicated generally at 51.

Operation will be apparent from examination of tank pair 45, i.e., tanks 36 and 37. Referring to FIG. 1, inlet feed manifold 50 extends from inlet 10, bringing air to be treated from the process. At joint 55, line 56 engages manifold 50, directing air through tanks 36 and 37. Line 56 includes a first segment 57, having control valve 58 therein. Segment 57 is directed into the top of tank 36. Off-gases from tank 36 are removed from bottom outlet 60 and are directed by pipeline segment 61 into the top of tank 37. Off-gases from tank 37 are removed from bottom outlet 64 and are directed through segment 65, through control valve 66, to joint 67. At joint 67, the off-gases are directed to outlet feed manifold 51.

Sampling ports are indicated generally at 69. The sampling ports can be used to check such parameters as air temperature, velocity, volumetric flow rate, and pressure drop across various points in the system.

Analogously, tank pair 46 is positioned in line 71 and tank pair 47 is positioned at line 72.

Attention is directed to ends 75 and 76 of manifolds 50 and 51, respectively. Each of ends 75 and 76 is capped by caps 80 and 81, respectively.

In general, biomass filtration system 29 can be readily expanded to handle still more air passage therethrough, for example by extending manifolds 50 and 51 to accommodate still more tanks.

Throughout biomass filtration unit 29 are located control valves 85 and ports 86, for easy control and sampling. Through appropriate operation of the valves, any of tanks 36–41 can be isolated and taken off line for service or replacement. For the arrangement shown in FIG. 1, each of tanks 36–41 is depicted positioned on a pallet 90, for ease of movement. The pipes used throughout the system would preferably include appropriate joints, etc. that can be easily disconnected to facilitate this operation.

In general, it may be desirable to intermittently, or even continuously, introduce water and/or other nutrients into selected ones of tanks 36–41. An optional line for accommodating this with respect to tank 40 is indicated generally in FIG. 1 at 95 (in phantom). Of course a similar line could, optionally, be used with each tank.

Still referring to FIG. 1, airflow from outlet manifold 51 is directed into water remover 22. The particular remover or separator 22 shown comprises a pair of tanks 101 operated with appropriate float water controls, in a conventional manner, to control water depth. Outlet air flow from moisture separator 22 is indicated at 102, with the air being directed outwardly from the biomass filtration system 29 to downstream particle filter 23. A conventional particle filter arrangement may be used.

Figure 2:
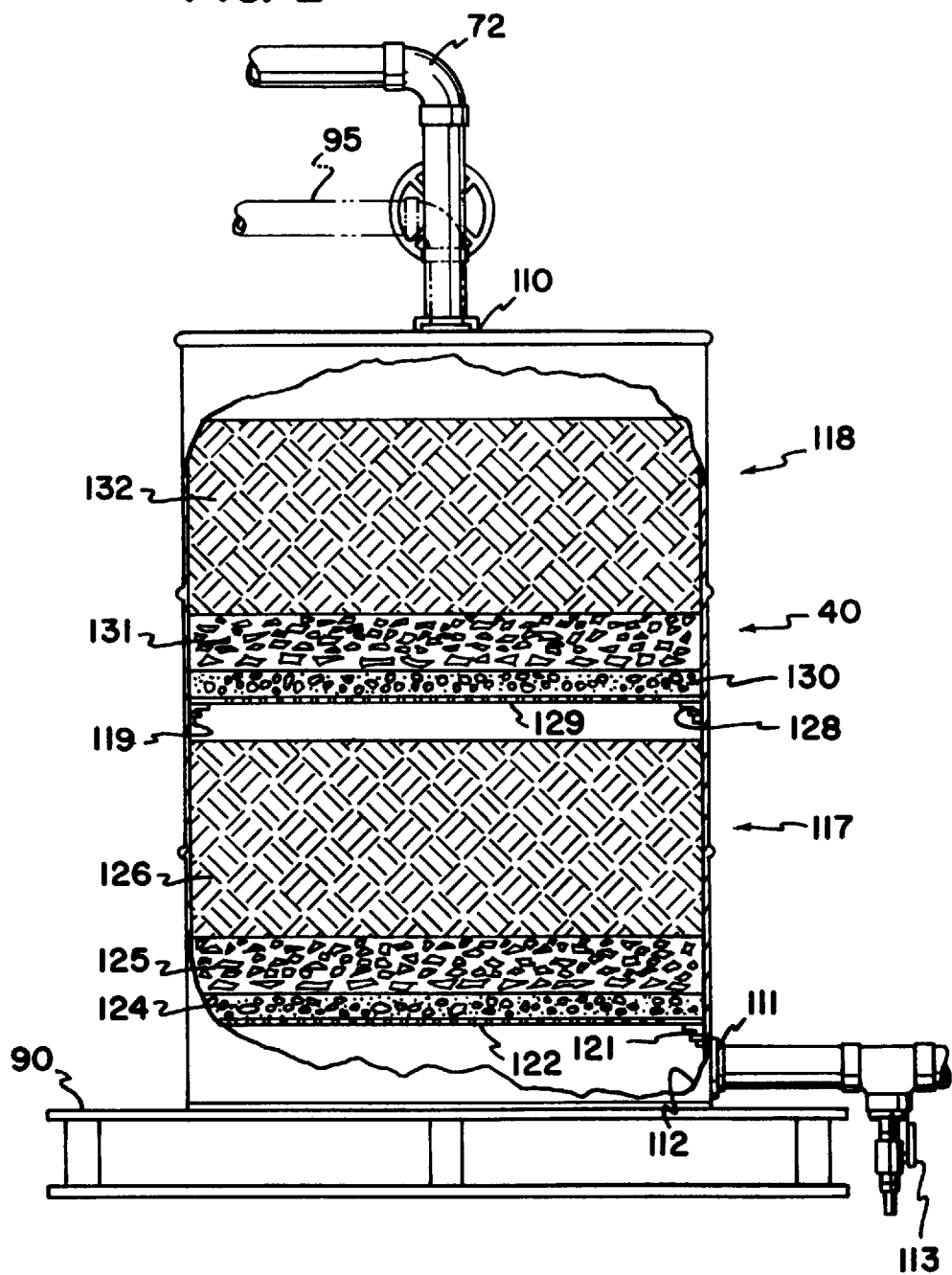
FIG. 2 is a fragmentary, side elevational view of a biomass filtration tank utilized in FIG. 1.

Attention is now directed to FIG. 2. In FIG. 2, a side elevational view of tank 40 is provided. The view in FIG. 2 is with portions broken away to indicate internal detail.

Referring to FIG. 2, tank 40 is depicted with inlet segment 72 directed into a top portion 110 thereof. Air outlet 111 of tank 36 is oriented in a lower region 112 below any material packed within the tank 36. Should any water collect in the lower region 112 of tank 36, it can be removed through drain 113. In FIG. 1 water drains from the tanks are fed into recirculation lines 114, and back to evaporator 11.

Still referring to FIG. 2, the bed in the interior of tank 40 is generally stratified for advantageous biofiltering operation. In general, the bed in tank 40 is divided into a lower stratified region 117 and an upper stratified region 118. The stratified regions 117 and 118 are separated by open space 119. Separation of the bed in tank 40 into upper and lower stratified regions 118 and 117, respectively, inhibits the likelihood of channeling through the biomass and ensures good porosity.

Still referring to FIG. 2, tank 40 includes internal lower bracket 121 on which porous grate or screen 122 is positioned. Porous screen 122 prevents biomass material (or packing material, i.e. the bed) from settling into lower region 112. For the particular treatment tank 40 shown, above porous screen 122 is located a bed comprising a region or strata of volcanic rock 124, above that a porous region or strata 125 of wood or bark chips mixed with soil, and above that a region or strata 126 containing a bacteria-loaded mixture of peat, topsoil, vermiculite, and some bark. A variety of packing materials may be used, however.

In general, the upper stratified region 118 is analogous, comprising bracket 128, porous screen 129, strata of volcanic rock 130, strata of wood or bark chips mixed with soil 131 and strata 132 of topsoil, vermiculite, bark, and peat. Such a mix is good for a high flow, wet, air stream since it resists packing.

Again, a variety of materials can be utilized to form the "bed" or "beds" of tank systems according to the present invention. The particular examples given for tank 40, with upper and lower separated stratified regions 117 and 118 with some head space between the beds, are particularly useful for avoiding undesirable packing, maintaining air flow and maintaining a desired porosity. Variations may be desired to handle selected airflows, purification rates or particular contaminants. Generally, in preferred arrangements each bed (or sub-bed) is at least one-foot thick; and, if more than one bed is positioned in a single tank, preferably the total thickness of all beds therein is at least two-feet. In this context, the thickness (sum) of the beds is inclusive of all materials and layers therein; i.e. rock, bark chips, soil, etc.

Still referring to FIG. 2, tank 40 is provided with optional nutrient or water inlet 95, indicated in phantom lines.

It is an advantage of arrangements according to the present invention that a wide variety of tanks may be used. A reason for this is that the arrangement generally operates under vacuum relative to ambient, and thus tanks and lines which can accommodate substantial pressures therein are not required.

The particular system depicted in the schematics of FIGS. 1 and 2 is shown utilizing stainless steel drums. The particular drums depicted are 85 gallon salvage drums (27 inch diameter, 36 inches deep), the interiors of which have been coated with enamel to resist corrosion.

Referring to FIG. 1, two different sized airflow pipes are shown. For an example, the larger pipes, comprising manifolds 50, 51 can be Schedule 40 PVC (polyvinyl chloride) 4 inch diameter pipes; and, the smaller pipes, for example pipes 56, 71, 72 can be Schedule 40 PVC 2 inch diameter pipes.

The pipes 136, 137, making the immediate connections to the blower 25, are preferably galvanized steel piping (for example, 2.5 inch diameter). A reason for galvanized steel piping at this location is that in the immediate vicinity of the blower 25, substantial heat may be generated in the air stream, which can damage PVC piping.

The particular arrangement shown in the schematic of FIG. 1, made with equipment of the size indicated in the previous three paragraphs, is configured for an air flow of up to about 450 ACFM. It can readily be operated with a commercially available, 10 horsepower, regenerative blower. It can readily withstand operation with a pressure drop, across the system, of up to about 40 inches of water. It will be preferred to construct the arrangement for operation with a pressure drop across the system of about 20 inches of water or less. It is an advantage to arrangements of the present invention that they can be constructed to withstand such vacuum draws, while using readily available and relatively inexpensive components.

In general, the grate or screen (122, 129) positioned within the tanks should be a relatively strong material, for example steel which has been appropriately coated to reduce rusting. Alternatives can be used, however.

A variety of additional equipment can be used in association with arrangements according to the present invention, to facilitate operation. For example, various thermocouples can be used in association with the tanks to allow for monitoring of bed temperature. Also, various pressure gauges 138, etc. can be used to monitor operation.

As will be apparent from the review with respect to FIG. 1, biomass systems in arrangements according to the present invention are made relatively porous, with porosity enhanced by the use of filler such as volcanic rock, gravel, wood chips or similar material in the bed. This is advantageous in many systems according to the present invention, especially those in which the flow rate is relatively high, since it helps ensure that a good air flow rate under the vacuum draw can be readily obtained without development of a substantial pressure drop across the bed.

Example of an Arrangement for High Flow Operation

Figure 3:
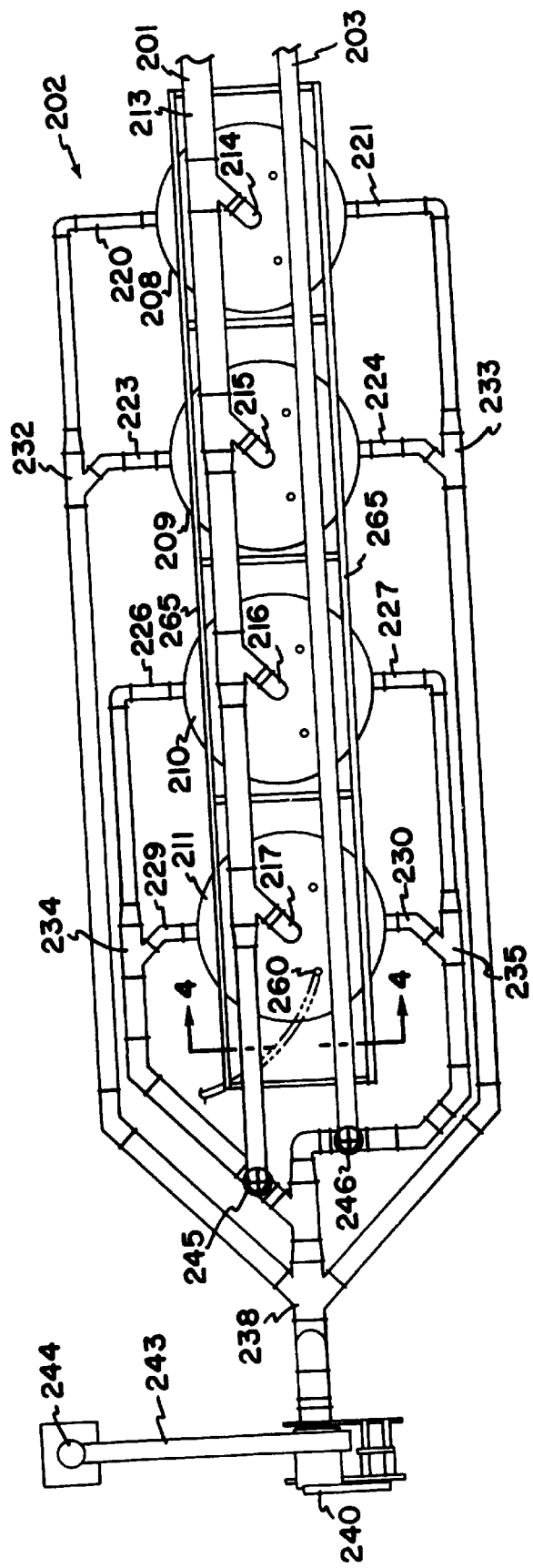
FIG. 3 is a fragmentary, top schematic representation of an alternate biomass air filtration system according to the present invention.

Attention is now directed to the schematic of FIG. 3. In this schematic, the principles of the present invention are depicted embodied in an arrangement for handling an even higher flow (volume) of air to be treated, therethrough. The particular arrangement shown will readily handle a flow up to about 7500 ACFM. This can be accomplished in some systems incorporating the principles of the present invention, through use, as a blower, of an industrial fan rated for 25 horsepower operation.

The particular schematic of FIG. 3 was designed for operation to treat odoriferous off-gases from partially composted municipal trash. In particular, this waste will typically be positioned in aeration trays, in an isolated building, for passage of air therethrough to remove volatiles. In the schematic of FIG. 3, the building for aerating the partially composted waste is not shown. Air flow from the building to the biofilter system 202 for treatment is shown at line 201. Line 203 is a bypass line, for air drawn from the aerating building to bypass the biofilter system.

The biofilter system 202 of FIG. 3 generally comprises four treatment tanks 208, 209, 210 and 211. For the configuration of air flow of system 202, air only passes through one of the tanks 208–211, during treatment. That is, the air flow stream is divided up into four substreams, and each substream passes through only one tank. Alternately phrased, the tanks 208–211, are operated with air flow in parallel, rather than series. Thus, all four tanks are simultaneously used, but any given volume of air only passes through one tank.

Still referring to FIG. 3, reference 213 indicates the inlet manifold for air to be filtered. Spur lines 214–217 direct air from inlet manifold 213 into each of tanks 208–211, respectively. As with the arrangement of FIG. 1, the air passes downwardly through each of the tanks 208–211 in operation.

Each of tanks 208–211 includes two outlets positioned in the bottom thereof, for air to be removed. Outlet lines for tank 208 are indicated at 220 and 221. Analogously, the outlets for tank 209 are indicated at 223, 224; the outlets for tank 210 at 226, 227; and, the outlets for tank 211 at 229 and 230.

In preferred systems for high flow operation, it will be preferred to use a smooth pipe material without square turns, to avoid unnecessary contribution to the pressure differential resulting from friction between the air and the piping. It will also be preferred to use piping which is resistant to corrosion or moisture deterioration. Smooth PVC piping has been found to be useful.

Referring to the schematic of FIG. 3, outlets 220 and 223 from tanks 208 and 209, respectively, join at manifold 232, for removal. Similarly, outlets 221 and 224 join at manifold 233; outlets 226 and 229 join at manifold 234; and outlets 227 and 230 join at manifold 235. Manifolds 232, 233, 234 and 235 ultimately join at outlet trunk 238, for withdrawal of air from the biofilter system 202, to the operating fan or blower 240 (i.e. air draw apparatus).

From the operating fan or blower 240, the air is exhausted through line 243 and stack 244.

Various valves, such as indicated at 245, 246, provide for selected operation. An optional hose connector for connecting a water/nutrient line is shown on tank 211 at 260. Similar hose connectors can be used with respect to each tank.

Each of the tanks 208–211 can include an optional liquid drain in the bottom thereof, appropriately valved for operation. It has been found, however, that in general operation can often be conducted without the need for utilization of the drains, provided the amount of moisture introduced into each tank can be balanced with the rate of air flow such that moisture loss from standing water in the bottom of the tank approximately matches its introduction.

Figure 4:
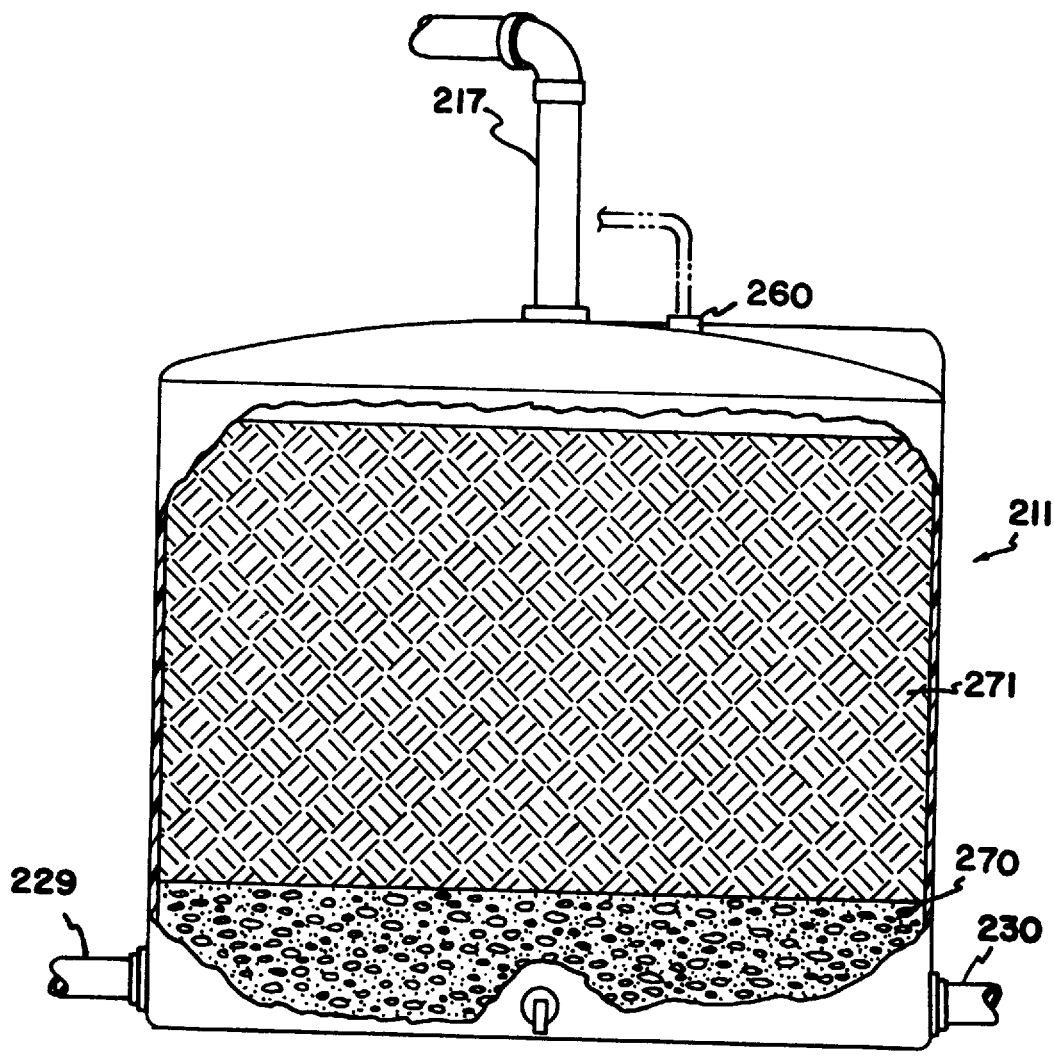
FIG. 4 is a fragmentary, side elevational view of a biomass filtration tank utilized in FIG. 3.

The system of FIG. 3 was designed to be operable, if desired, with utilization of 9000 gallon PVC agricultural drums, which, at the end of their use on a farm would otherwise have been discarded. The tanks depicted in FIGS. 3 and 4 are such PVC agriculture drums, each of which includes a filling spout (see FIG. 4). It was also designed to utilize PVC pipe (various sizes from about 12 inches to about 26 inches in diameter depending on flow requirements) generally throughout, except in the immediate vicinity of the blower and downstream therefrom, at which point steel would likely be used.

In general, such plastic components utilized for tanks in a system operating under vacuum, will implode if the pressure head within the system is at about 20 inches of water or greater. The overall system was designed to handle a relatively high flow of air, for treatment, with a total pressure drop across the system never being held at much greater than about 14 or 15 inches of water. Thus, the system can be readily operated, efficiently, for air treatment, without the need for reinforced structure to withstand the vacuum therein.

It is noted that the tanks in the schematic of FIG. 3 could be enclosed within a building. In general, composting generates heat. It is believed that for many environments the heat generated by the composting will warm the air sufficiently, to maintain a stable bioreactor, provided, at least for the winter, the tanks are simply enclosed within a shelter. However, heaters or other systems to maintain reactor bed stability may be used. Also various control valves, monitors, sample ports, etc. (not shown) could be used. At 265 a framework, for support of certain components of the system, is shown.

For the particular preferred arrangement shown, it is important to operate the system with packing in the tanks being no greater than will allow for ready flow of air thereacross, without development of a pressure differential above about 14–15 inches of water. For the system shown, this is conducted by filling each of the tanks in a preferred manner, for example as shown in FIG. 4.

Referring to FIG. 4, treatment tank 211 is depicted. It is shown with portions broken away, so that internal arrangements can be depicted. In the bottom of the tank, there is a layer 270 of about 2 feet of washed river rock, which generates a good air flow distribution in the bottom of the tank. It is foreseen that in operation typically about 2 inches of water will stand in the bottom of the tank. As indicated above, an optional drain can be used in the bottom of the tank, to ensure appropriate moisture level.

Above the rock, a porous mixture 271 containing the microorganisms to conduct the treatment, is positioned. The particular bacteria-loaded mix shown comprises a mix of peat, compost, vermiculite, and pinebark. The large pieces of pinebark and vermiculite ensure the appropriate porosity of the system.

Selection of Biomass Bed Material

The design of filter media for biofilters is variable depending on the importance of a number of design criteria. A principal criteria for the design of a biofilter which involves a pressure of less than ambient (i.e. vacuum) is the porosity of the overall biofilter bed. Porosity is important because adequate flow through the bed must be maintained. Adequate flow through the bed determines the size of the blower and the ultimate volume of air that can be moved through the system. The downward flowing air current of the described system has the potential effect of compacting the biofilter bed. Thus the biofilter bed should be designed to resist compaction that would undesireably reduce the porosity and the ultimate gas flow rate through the system.

Another important design criteria for the biofilter media is the surface area available for the bacteria in the biomass to adhere. Gas entering the system should come into contact with the greatest amount of bed material surface area reasonably possible, to effect the highest obtainable removal rates. As the contaminants in the gas stream enter the system, they are adsorbed into minute quantities of water that partially fill the porous structure of the biofilter media. The bacteria cultures exist in abundance on the surfaces of these water films. Digestion of the contaminants that dissolve in the water films is a primary method of biodegradation (and thus filtering) in the described biofilter.

Other important design criteria include: the organic material available to the bacterial cultures as nutrients, the ability of the media mix to self regulate or buffer pH, the ability of the media to support its own weight without compacting, the presence of indigenous bacteria in the biofilter material, the cost of the media, the availability of the media in bulk quantities, and the relative ease of handling (transporting, loading and unloading the biofilter).

Based on these basic design criteria, an optimum biofilter media can be constructed to meet the requirements of a wide variety of systems. The following list presents sample media components that can be used to construct the biofilter media. Of course the list is exemplary only, not exhaustive.

| Biofilter Media Component | Principal Benefit |
|---|---|
| Coarse Hardwood Bark (3" cross-sectional diameter) | Increase porosity of biofilter, good surface area, resists physical degradation, low cost, readily available, light weight, absorbs water. |
| Peat (non-sterilized) | High organic content, very light, relatively inexpensive, readily available. |
| Vermiculite | Bulking agent, high surface area, resists physical degradation, very light, somewhat available. |
| Pearlite | A type of obsidian. Has a high surface area and operates as a bulking agent. |
| Top Soil (non-sterilized) | High organic content, readily available, indigenous bacteria cultures, absorbs water, low cost. |
| Activated Carbon | Bulking agent, relative low cost (spent), very porous, may absorb some contaminants, buffering ability, odor buffering. |
| Oyster Shell | pH buffering ability, relatively porous |
| Lime | pH buffering ability, may stabilize some contaminants, readily available, low cost, odor buffering. |
| Compost | High organic content, readily available, indigenous bacteria cultures, bulking agent, absorbs water. |
| Pea gravel | Filter material, prevents particulate escape, supports biofilter, stable, low cost, high surface area. |
| Bulking agents (plastic formed column packing media) | Bulking agent, increases porosity and surface are, stable. |
| Manure (non-sterilized) | High organic content, indigenous bacteria cultures, readily available. |
| Volcanic Rock | Filter material, prevents particulate escape, supports biofilter material, relatively low weight, high porosity, readily available. |

In instances where the soil has a high clay content, or is very fine, it may be desirable to ensure that a substantial amount of bulking agent or filler is mixed with it, to avoid compaction in use.

The media that was selected for the biofilter of FIGS. 1 and 2 was composed of top soil, vermiculite, volcanic rock, large hardwood bark, and peat. Each drum held approximately 8 cubic feet of media (not counting the volcanic rock) in two discrete beds. The approximate formulation for the media was:

| Large hardwood bark chips | 4 cubic feet |
|---|---|
| Topsoil | 2 cubic feet |
| Peat | 1 cubic foot |
| Vermiculite | 1 cubic foot |

The media was mixed by hand in a 3 yard "roll off" container with a shovel. In the material immediately above the volcanic rock, a higher percent of bark chips was used, than in higher layers, to help ensure porosity. When the desired consistency was reached, the material was transferred to the drums using shovels and scoops. The material was deposited onto a layer of approximately 2 inches of volcanic rock at the bottom of the drum. The media was added until the top of the first bed nearly reached the intermediate drum supporting screen. The second layer was constructed in the same manner over 2 inches of volcanic rock on the intermediate supporting screen to within 3 inches of the top of the drum.

The main design criteria for the biofilter media for this system was porosity, organic content, availability, and low cost. This biofilter when tested achieved a measured removal efficiency in excess of 95% for formaldehyde.

The media selected for the biofilter of FIGS. 3 and 4 was composed of washed river rock, peat, top soil, vermiculite, compost and coarse hardwood bark. Each biofilter vessel held approximately 21.25 cubic yards of media in one layer atop washed river rock. The approximate formulation of the media was:

| Large hardwood bark chips | 8.5 cubic yards |
|---|---|
| Topsoil | 7.0 cubic yards |
| Peat | 3.5 cubic yards |
| Vermiculite | 1.25 cubic yards |
| Compost | 1.0 cubic yards |

The media was constructed by first establishing stockpiles of the materials in the staging area. Materials were spread out by a front-end loader in long windrows and thoroughly mixed together using a Scarab compost turner. When the appropriate mixture was reached, the material was conveyed into the top of each biofilter vessel atop approximately 2 feet of washed river rock. The biofilter media was added to a depth of 8 feet in each vessel.

The main design criteria for the biofilter media for the system of FIGS. 3 and 4 was extremely high porosity, resistance to compaction, organic content, moisture holding capability, availability, and low cost. The efficiency of this biofilter has been demonstrated by the absence of odors and odor complaints at a facility when installed for testing.

Engineering Considerations

The following recitations indicate engineering considerations and analyses useful in developing specific arrangements, for the test circumstances reflected by the Figures. The considerations will be useful in developing a particular biofilter arrangement according to the present invention, for installation in other situations.

EXAMPLE 1

The Biofilter Design of FIGS. 1 and 2

The design of the experimental pilot scale biofilter of FIGS. 1 and 2 began with a study to investigate the options for treating formaldehyde emissions from an evaporative waste water system. Formaldehyde is an organic contaminant that has a low Henry's law constant ($5.8 \times 10^{-5}$) which means that generally it is very soluble in water. Compounds that are soluble in water will work well with biofilters due to the fact that the bacteria that digest these contaminants exist in the thin film aqueous environment.

For this biofilter, it was determined that formaldehyde would be readily adsorbed by the system and broken down by the microorganisms indignant to the biofilter. Additional contaminants such as particulate, metals or certain toxic organic and inorganic substances can effectively preclude untreated gaseous waste streams from biofiltration. There were no contaminants in the waste water to be treated by this system that would have a deleterious effect on the system or the microorganisms in the system.

The general principles of filter design considerated for this project were similar to those reported below for Example 2.

The total volume of the air that would need to be removed from the waste water evaporation tray was a function of the total volume of the venting hood and the tray (100 CF) and the number of desired air exchanges per unit of time. Based on the total volume of the evaporative tray and hood assembly, the minimum air flow through the system would be approximately 350 CFM. Based on this flow rate, the hood would be kept under slight negative pressure, thus not allowing formaldehyde emissions to escape. The hood formed a tight seal over the evaporative tray thus the ability of the system to collect odors (capture efficiency) was assumed to be 100%.

The volume of the biofilter media was calculated based on the velocity of gas that would be passed through the system, and the desired contact time of the gas and the biofilter media. Contact times for various biofiltration systems have been related to biodegradation rates for certain contaminants. Generally, the higher the biodegradation rate, the faster the air flow through the system (holding efficiency constant). The biodegradation rate for formaldehyde is relatively high $1.39 \times 10^{-6}$) which means that the air flow through the system and thus the residency time could be reduced relative to systems designed to handle other contaminants. The initial contact time chosen for this biofilter was approximately 10 seconds which, according to emissions testing, provides for adequate reaction time. The thicker beds of the negative pressure modular biofilter allow for more media to come into contact with the contaminants as they pass through the system, thus offsetting reductions in actual contact time while allowing velocities to increase. The net effect is that a smaller biofilter can treat more gas more efficiently. The volume of this biofilter was sized to fit into six 85 gallon drums each with an internal volume of approximately 10 cubic feet. The drums were painted on the inside with epoxy paint to resist corrosion.

After the type and size of the biofilter was selected, the blower was selected. The selection of the type and size of fan is dependent upon the maximum air flow rate desired, the anticipated pressure drop in the system due to the biofilter bed and the associate piping, the energy usage and economics of the blower, the physical size and energy requirements of the blower, and the blower materials. For this project, the pressure drop across the system was estimated using the pressure loss nomegraphs for the piping distributors, and an estimate of pressure drop through the biofilter beds. Pressure loss through a biofilter bed can be estimated using the formula described in Example 2, for the biofilter design of FIGS. 3 and 4.

The maximum expected pressure drop of this system was 25 inches. The biofilter exit gas was assumed to be dry, at ambient temperature and noncorrosive. The biofilter would have the effect of buffering the pH of the incoming waste water vapor and stabilizing the temperature. The blower that was chosen for this site was a 10 hp regenerative blower designed to provide for approximately 450 CFM against a vacuum head of up to 60 inches of water, in a slightly corrosive environment. Regenerative blowers are more efficient in moving air against a high vacuum than other types of blowers or fans. Regenerative blowers are also quite durable and low maintenance. The blower was modified on-site to match the ducting of the biofilter and the discharge stack.

Piping was selected for the biofilter that would be low cost, easily handled by the construction crew, resistant to weather and the expected corrosive nature of the biofilter inlet gas. The piping that was selected for this system was available through a local supplier thus reducing the delivery costs and the lead time for ordering.

Initial emission testing of this pilot scale biofilter indicated that the removal efficiency of the system was over 95% for formaldehyde.

EXAMPLE 2

The Biofilter Design of FIGS. 3 and 4

The design of the biofilter began with an identification of the contaminant to be removed by the system. In this case, the principal contaminant that was to be removed from the gas stream was odors from a municipal trash composting facility. Odors are complex in nature and are generally not attributed to any one chemical compound. Odors from composting facilities, however, have been characterized in the literature. The major components of the odors can (typically) include: hydrogen sulfide ($H_2S$), di- and trimethyl sulfide and disulfides, ammonia ($NH_3$), odorous amines ($C_2H_3NH_2$), short-chain fatty acids, and aldehydes and mercaptans. Odors and odorous compounds have been, in some systems, effectively treated by biofilters of various designs, for over 50 years.

The actual designing of the biofilter began with determining the volume of material that would be needed in the system, the amount of time that the gas bearing the contaminant must be in contact with the biofilter media, the pressure drop associated with the biofilter media and associated piping, the physical properties and requirements for gas conditioning, the site parameters for siting the biofilter, cost and permitting considerations and the desired removal efficiency for the system.

For this biofilter system, it was initially determined that the odors and the odorous compounds from the facility could be readily addressed by a biofilter. This decision was based on the fact that composting facilities have used biofilters in the past to successfully treat odors from some composting facilities. There was nothing unusual or unique in the site or the operation of the composting facility that would have precluded the use of a biofilter with the possible exception of extreme cold conditions sometimes experienced during the winter. Upon interviewing the site personnel, it was learned that odors were not considered a problem at the facility during the winter months. Furthermore, the biofilter that would eventually be proposed (negative pressure, modular, topdown flow) could be situated near the main composting building due to its compact size and thus receive heat from the building to keep the media active, if winter operation became a desired design parameter.

The total volume of the air that would need to be removed from the composting building to keep them under negative pressure and prevent odors from escaping was the next design parameter. Based on the total volume of the interior of the building and the desired number of air exchanges per hour, it was determined that the minimum air flow through the system would be approximately 6500 CFM. Based on this flow rate, the building would be kept under slight negative pressure, thus not allowing odors to escape. This design criteria was predicated on the ability of composting building to effect an efficient seal over the compost.

The volume of the biofilter media was calculated based on the velocity of gas that would be passed through the system, and the desired contact time of the gas and the biofilter media. This relationship can be expressed in the following equation:

$$\text{Volume (ft}^3\text{)}=\text{Desired contact time (sec)} \times \text{Flow rate (CFM)}$$

Contact time for biofiltration of odors have been investigated by a number of researchers and generally range from a few seconds to over 1 minute. The contact time chosen for this biofilter was approximately 20 seconds which was believed to be sufficient to provide for adequate reaction time. The relatively thick beds of a negative pressure modular biofilter, according to the present invention, allow for more media to come into contact with the odors as they pass through the system, thus offsetting reductions in actual contact time while allowing velocities to increase. The net effect is that a smaller biofilter can treat more gas more efficiently. The volume of this biofilter was designed to fit into eight 9000 gallon tanks each with an internal volume of approximately 25 cubic yards. Due to financial constraints, only four tanks were initially installed, as shown in FIG. 3. It is anticipated that expansion may eventually be conducted.

After the type and size of the biofilter has been selected, the blower or fan must be selected. The selection of the type and size of fan is dependent upon the maximum air flow rate desired, the anticipated pressure drop in the system due to the biofilter bed and the associate piping, the energy usage and economics of the blower, the physical size and energy requirements of the blower, and the blower materials. For the project of FIG. 3, the pressure drop across the system was estimated using the pressure loss nomegraphs from the piping distributors, and an estimate of pressure drop through the biofilter beds. Pressure loss through a biofilter bed can be estimated using the following formula:

$$\frac{\Delta P}{ft} \alpha \frac{\text{Vapor flow rate }(CFM)}{\text{Cross-sectional Area }(ft^2)}$$

The maximum expected pressure drop of this system was 15 inches of water. The biofilter exit gas was assumed to be dry, at ambient temperature and non-corrosive. The biofilter would have the effect of buffering the incoming compost odors, removing moisture from the gas and stabilizing the temperature.

In the area in which the biofilter was to be installed, there was an energy credit for blowers and motors that achieved a certain efficiency of operation. The blower that was chosen for this site was a large industrial 25 hp fan designed to provide for approximately 7500 CFM against a vacuum head of up to 20 inches of water, in a slightly corrosive environment. The motor for the fan met the energy efficiency requirements of the location and was in stock at the time of the order. The fan was modified on-site to match the ducting of the biofilter and the discharge stack. Piping (PVC) was selected for the biofilter that would be low cost, easily handled by the construction crew, resistant to weather and the expected corrosive nature of the biofilter inlet gas. The piping connections were selected to reduce the amount of pressure loss that would be attributed the entire gas transmission system. The piping that was selected for this system was available through a local supplier thus reducing the delivery costs and the lead time for ordering.

What is claimed is:

1. A method of treating air for reduction of a presence of contaminating material therein; said method comprising steps of:
   (a) directing air to be treated into a first bioreactor treatment tank;
      (i) the first bioreactor treatment tank having at least one bioreactor bed, a closed top, a closed bottom and a sidewall; said closed top and sidewall defining an enclosed head space above the at least one bioreactor bed;
      (ii) said step of directing air to be treated comprising directing air into the enclosed head space and above the at least one bioreactor bed; and,
   (b) drawing air from the enclosed head space downwardly through said at least one bioreactor bed;
      (iii) said step of drawing being conducted under an air pressure, within said at least one bioreactor bed, of less than ambient.

2. A method according to claim 1 wherein:
   (a) said step of drawing air downwardly through said at least one bioreactor bed comprises passing air downwardly through at least one bioreactor bed which is at least one foot thick.

3. A method according to claim 1 further comprising a step of:
   (a) directing air, after it has been passed through the at least one bioreactor bed, through an exhaust stack arrangement.

4. A method according to claim 1 further comprising steps of:
   (a) directing air which has been drawn downwardly through said at least one bioreactor bed into an enclosed head space above at least one bioreactor bed in a second treatment tank; and,
   (b) drawing air from the enclosed head space in the second treatment tank downwardly through the at least one bioreactor bed therein;
      (i) said step of drawing being conducted under an air pressure, within the second treatment tank, of less than ambient.

5. A method according to claim 1 further comprising a step of:
   (a) feeding water into the at least one bioreactor bed in the treatment tank during said step of drawing air downwardly therethrough.

6. A method according to claim 5 wherein:
   (a) said step of feeding water comprises feeding water downwardly into the at least one bioreactor bed.

7. A method according to claim 1 further comprising a step of:
   (a) feeding nutrient material into the at least one bioreactor head in the treatment tank during said step of drawing air downwardly therethrough.

8. A method according to claim 7 wherein:
   (a) said step of feeding nutrient material comprises feeding nutrient material downwardly into the at least one bioreactor bed.

9. A method according to claim 1 wherein:
   (a) said step of drawing air downwardly through the at least one bioreactor bed comprises drawing air downwardly through at least one bed comprising active bacteria-loaded material positioned above lower strata comprising rock.

10. A method according to claim 1 wherein:
    (a) said step of drawing air downwardly through at least one bioreactor bed comprises drawing air downwardly through at least one bed comprising wood or bark chips.

11. A method according to claim 1 wherein:
    (a) said step of drawing air downwardly through at least one bioreactor bed comprises drawing air downwardly through at least one bed comprising wood or bark chips mixed with soil.

12. A method of treating for reduction of a presence of contaminating material therein; said method comprising steps of:
  (a) directing air to be treated into an enclosed head space of a treatment tank above at least one bioreactor bed; and
  (b) drawing air from the enclosed head space downwardly through said at least one bioreactor bed;
    (i) said step of drawing being conducted under an air pressure, within said at least one bioreactor bed, of less than ambient;
  (c) wherein said method is conducted upon air to be treated, when it is directed into said head space, having a first contaminant level, until a contaminant level in the air is reduced by at least 80%, through bioreactor treatment.

13. A method according to claim 12 wherein:
  (a) said treating is conducted until a contaminant level in the air is reduced by at least 90%, through bioreactor treatment.

* * * * *